(12) United States Patent
Klimko et al.

(10) Patent No.: US 6,680,339 B2
(45) Date of Patent: *Jan. 20, 2004

(54) 15-FLUORO PROSTAGLANDINS AS OCULAR HYPOTENSIVES

(75) Inventors: Peter G. Klimko, Fort Worth, TX (US); Mark R. Hellberg, Highland Village, TX (US); Paul W. Zinke, Fort Worth, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 67 days.

This patent is subject to a terminal disclaimer.

(21) Appl. No.: 10/100,399

(22) Filed: Mar. 18, 2002

(65) Prior Publication Data

US 2002/0151587 A1 Oct. 17, 2002

Related U.S. Application Data

(63) Continuation-in-part of application No. 09/284,432, filed as application No. PCT/US97/20671 on Nov. 7, 1997.
(60) Provisional application No. 60/030,519, filed on Nov. 12, 1996.

(51) Int. Cl.[7] ............... A61K 31/216; A61K 31/5575; C07C 69/618
(52) U.S. Cl. ............... 514/530; 514/573; 560/121; 562/503
(58) Field of Search ............... 560/121; 562/503; 514/530, 573

(56) References Cited

U.S. PATENT DOCUMENTS

| | | | |
|---|---|---|---|
| 4,425,359 A | | 1/1984 | Pellegata et al. |
| 4,599,353 A | | 7/1986 | Bito |
| 4,665,214 A | * | 5/1987 | Bezuglov et al. ......... 560/121 |
| 5,321,128 A | | 6/1994 | Stjernschantz et al. |

FOREIGN PATENT DOCUMENTS

| | | |
|---|---|---|
| DE | 42 29 050 A1 | 3/1994 |
| EP | 0 308 135 A2 | 3/1989 |
| EP | 0 435443 A2 | 7/1991 |
| EP | 0 561 073 A1 | 9/1993 |
| EP | 0 639 563 A2 | 2/1995 |
| GB | 2146325 A | 4/1985 |
| JP | 7070054 A2 | 8/1993 |
| JP | 10087607 | 9/1996 |

OTHER PUBLICATIONS

Alm, *The Potential of Prostaglandin Derivatives in Glaucoma Therapy*, Current Opinion in Ophthalmology, 4(11):44–50 (1993).
Giuffre, *The Effects of Prostaglandin $F_2$ α the Human Eye*, Graefe's Archive Ophthalmology, 222:139–141 (1985).
Kerstetter et al., *Prostaglandin $F_2$ α–1–Isopropylester Lowers Intraocular Pressure Without Decreasing Aqueous Humor Flow*, American Journal of Ophthalmology, 105:30–34 (1988).
Lakin et al., *Effects of Fluorinated Prostaglandins on Platelet Aggregation*, Chemical Abstracts, vol. 121, abstract 50656 (1994).
Nakajima et al., *Effects of Prostaglandin $D_2$ and its Analogue, BW245C, on Intraocular Pressure in Humans*- Graefe's Archive Ophthalmology, 229:411–413 (1991).
Nigamatov et al., *Effect of 15–FluoroDderivatives of Prostaglandins $E_2$ and $_F 2α$ on Isolated Smooth Muscles*, Chemical Abstracts, vol. 112, abstract 30749 (1990).
Nigamatov et al., *Thromboxane $A_2$ –Like Activity of 11–Fluoro–11–Deoxyprostaglandin $F_2$ α on Isolated Smooth Muscles*, Chemical Abstracts vol. 105, abstract of 55217 (1986).

* cited by examiner

Primary Examiner—Kathleen K. Fonda
Assistant Examiner—Leigh C. Maier
(74) Attorney, Agent, or Firm—Barry L. Copeland

(57) ABSTRACT

15-fluoro substituted analogs of $PGF_{2α}$ and methods of their use in treating glaucoma and ocular hypertension are disclosed.

16 Claims, No Drawings

15-FLUORO PROSTAGLANDINS AS OCULAR HYPOTENSIVES

RELATED APPLICATION

This application is a continuation-in-part of U.S. patent application Ser. No. 09/284,432 filed Jun. 2, 1999, which is a national application under 35 USC §371 of PCT Application Serial No. PCT/US97/20671 filed Nov. 7, 1997, which draws priority from U.S. Provisional Application Ser. No. 60/030,519 filed Nov. 12, 1996, now abandoned.

BACKGROUND OF THE INVENTION

The present invention relates to compounds for the treatment of glaucoma and ocular hypertension. In particular, the present invention relates to the use of certain 15-fluoro analogs of F series prostaglandins to treat glaucoma and ocular hypertension.

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the flow of aqueous humor out of the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Some beta-blockers have increasingly become associated with serious pulmonary side effects attributable to their effects on beta-2 receptors in pulmonary tissue. Sympathomimetics may cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-Series prostaglandins (EP 0 561 073 A1). Of interest in the present invention are compounds which are believed to exhibit IOP lowering effects similar to those exhibited by $PGF_{2\alpha}$ (an F-series prostaglandin):

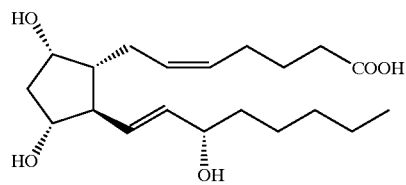

The relationship of $PGF_{2\alpha}$ receptor activation and IOP lowering effects is not well understood. It is believed that $PGF_{2\alpha}$ receptor activation leads to increased outflow of aqueous humor. Regardless of mechanism, $PGF_{2\alpha}$ and analogs have been shown to lower IOP (Giuffre, *The Effects of Prostaglandin $F_{2\alpha}$ the Human Eye*, Graefe's Archive Ophthalmology, volume 222, pages 139–141 (1985); and Kerstetter et al., *Prostaglandin $F_{2\alpha}$-1-Isopropylester Lowers Intraocular Pressure Without Decreasing Aqueous Humor Flow*, American Journal of Ophthalmology, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules lower IOP, many of these types of molecules have also been associated with undesirable side effects resulting from topical ophthalmic dosing. Such effects include an initial increase in IOP, breakdown of the blood aqueous barrier and conjunctival hyperemia (Alm, *The Potential of Prostaglandin Derivatives in Glaucoma Therapy*, Current Opinion in Ophthalmology, volume 4, No. 11, pages 44–50 (1993)).

Based on the foregoing, a need exists for the development of molecules that may activate $PGF_{2\alpha}$ receptors, yielding a more efficacious lowering of IOP, while exhibiting fewer or reduced side effects.

An agent which exhibits the same or improved efficacy, but with reduced side effects when compared to other agents, is said to have an improved therapeutic profile. It is an object of this invention to provide a class of IOP lowering agents with an improved therapeutic profile over $PGF_{2\alpha}$, and methods of their use. It has now unexpectedly been discovered that the presently claimed 15-fluoro analogs of $PGF_{2\alpha}$ meet this objective. While some prostaglandins with fluorine in the omega chain are known in the art [EP 435,443 A; JP 7,070,054 A2; *Eksp. Klin. Farmakol.*, volume 57, number 2, pages 39–41 (1994) (*Chemical Abstracts*, volume 121, abstract 50656 (1994)); *Izv. Akad. Nauk SSSR, Ser. Biol.*, volume 6, pages 831–7 (1989) (*Chemical Abstracts*, volume 112, abstract 30749 (1990))], the novel compounds of the present invention and their favorable therapeutic profiles in the treatment of glaucoma are neither disclosed nor suggested in that art.

SUMMARY OF THE INVENTION

The present invention is directed to compositions and methods of their use in treating IOP and ocular hypertension. In particular, the present invention provides 15-fluoro prostaglandin analogs believed to have functional $PGF_{2\alpha}$ receptor agonist activity, and methods of their use in treating glaucoma and ocular hypertension. As previously stated, the mechanism of action by which $PGF_{2\alpha}$ type prostaglandins lower IOP is not well understood. While the mechanism of action of the compounds of the present invention is not fully understood, the inventors theorize that such compounds exhibit enhanced FP receptor selectivity as a consequence of their decreased activity at the EP receptor site. While bound by no such theory, it is possible that an improved therapeutic index may result from a relative reduction of EP-mediated side-effects.

DETAILED DESCRIPTION OF THE INVENTION

It has unexpectedly been found that 15-fluoro substituted $PGF_{2\alpha}$ analogs of the present invention exhibit an improved therapeutic profile in the treatment of glaucoma and ocular hypertension when compared to natural prostaglandins and many of their known analogs. The substituted $PGF_{2\alpha}$ analogs of the present invention have the following formula I:

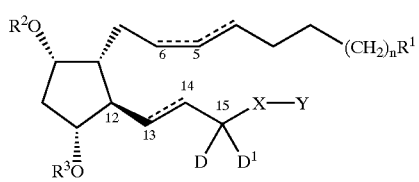

wherein:

$R^1 = CO_2R$, $CONR^4R^5$, $CH_2OR^6$, or $CH_2NR^7R^8$, where $R=H$ or cationic salt moiety, or $CO_2R$ = pharmaceutically acceptable ester moiety;

$R^4$, $R^5$ = same or different = H or alkyl; $R^6$ = H, acyl, or alkyl; $R^7$, $R^8$ = same or different = H, acyl, or alkyl; with the proviso that if one of $R^7$, $R^8$ = acyl, then the other = H or alkyl;

n=0 or 2;

- - - = single or non-cumulated double bond, with the provisos that a double bond between carbons 4 and 5 may not be of the trans configuration; and that a double bond between carbons 13 and 14 may not be of the cis configuration; $R^2$, $R^3$ = same or different = H, alkyl, or acyl;

D, $D^1$ = different = H and fluorine;

$X = (CH_2)_q$ or $(CH_2)_qO$; where q=1–6; and

Y = a phenyl ring optionally substituted with alkyl, halo, trihalomethyl, alkoxy, acyl, acyloxy, amino, alkylamino, acylamino, or hydroxy; or $X-Y = (CH_2)_pY^1$; where p=0–6; and

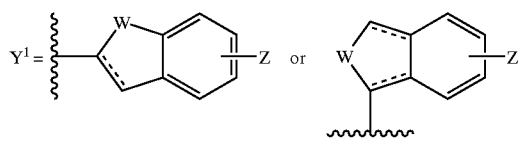

wherein:

W = $CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$ = H, alkyl, or acyl;

Z = H, alkyl, alkoxy, acyl, acyloxy, halo, trihalomethyl, amino, alkylamino, acylamino, or hydroxy; and

- - - = single or double bond.

For purposes of the foregoing definition, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e. non-toxic and non-irritating. Preferred among the ophthalmically acceptable esters are alkyl esters. Most preferred are $C_2$–$C_4$ alkyl esters, and especially isopropyl esters.

Preferred for use in the methods and compositions of the present invention are those compounds of formula I above, wherein:

$R^1 = CO_2R$, where R=H or $CO_2R$ = ophthalmically acceptable ester moiety;

n=0;

- - - = single or non-cumulated double bond, with the provisos that a double bond between carbons 4 and 5 may not be of the trans configuration; and that a double bond between carbons 13 and 14 may not be of the cis configuration;

$R^2 = R^3 = H$;

D = fluorine in the alpha (α) configuration, and $D^1$ = H in the beta (β) configuration;

X = $CH_2O$ or $CH_2CH_2$; and

Y = phenyl, optionally substituted with halo or trihalomethyl.

Especially preferred are those preferred compounds of formula I above, wherein: $R^1 = CO_2R$ and $CO_2R$ = lower alkyl (i.e., 1–6 carbons) carboxylic acid alkyl ester. Included in these especially preferred compounds are the following novel compounds:

| Compound Number | Compound Name | Compound Structure |
| --- | --- | --- |
| II | (5Z)-(9S,11R,15R)-16-(3-Chlorophenoxy)-9,11-dihydroxy-15-fluoro-17,18,19,20-tetranor-5-prostenoic acid isopropyl ester | 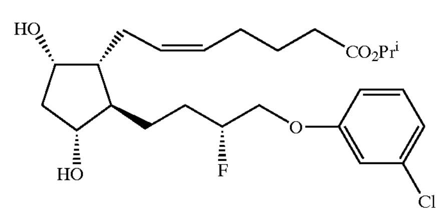 |
| III | (4Z)-(9S,11R,15R)-16-(3-Chlorophenoxy)-9,11-dihydroxy-15-fluoro-17,18,19,20-tetranor-4-prostenoic acid isopropyl ester | 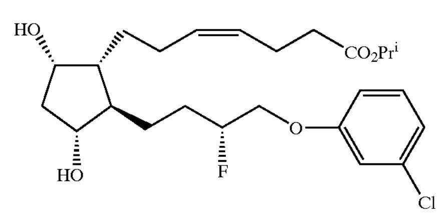 |

-continued

| Compound Number | Compound Name | Compound Structure |
|---|---|---|
| IV | (5Z)-(9S,11R,15R)-9,11-Dihydroxy-15-fluoro-16-[3-(trifluoromethyl)phenoxy]-17,18,19,20-tetranor-5-prostenoic acid isopropyl ester | 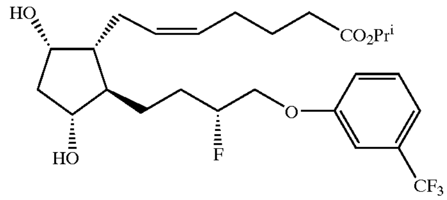 |
| V | (5Z)-(9S,11R,15R)-9,11-Dihydroxy-15-fluoro-16-phenoxy-17,18,19,20-tetranor-5-prostenoic acid isopropyl ester | 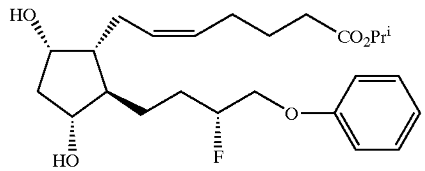 |

Included within the scope of the present invention are the individual enantiomers of the title compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials (*Asymmetric Synthesis* by J. D. Morrison and J. W. Scott, Eds., Academic Press Publishers: New York, 1983–1985 (five volumes) and *Principles of Asymmetric Synthesis* by R. E. Gawley and J. Aube, Eds., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed., VCH Publishers: New York, 1994; *Chiral Separations* by HPLC, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios.

In the foregoing illustrations, as well as those provided hereinafter, wavy line attachments indicate either the alpha (α) or beta (β) configuration. The carbon numbering is as indicated in the structural depiction of formula I, even when n=2. A hatched line, as used e.g. at carbon 9, indicates the α configuration. A solid triangular line, as used e.g. at carbon 12, indicates the β configuration. Dashed lines on bonds, e.g. between carbons 13 and 14, indicate a single or double bond. Two solid lines between carbons indicate a double bond of the specified configuration.

In the following Examples 1–4, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of II

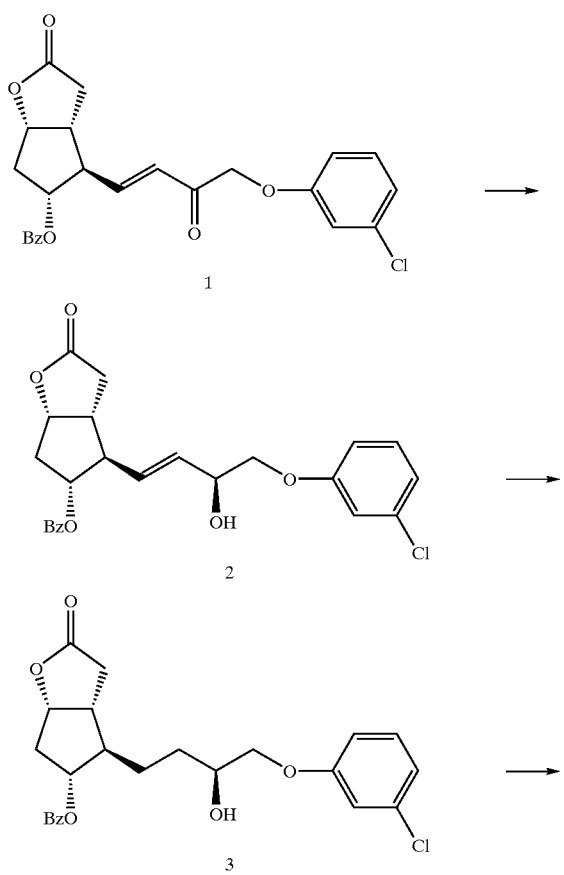

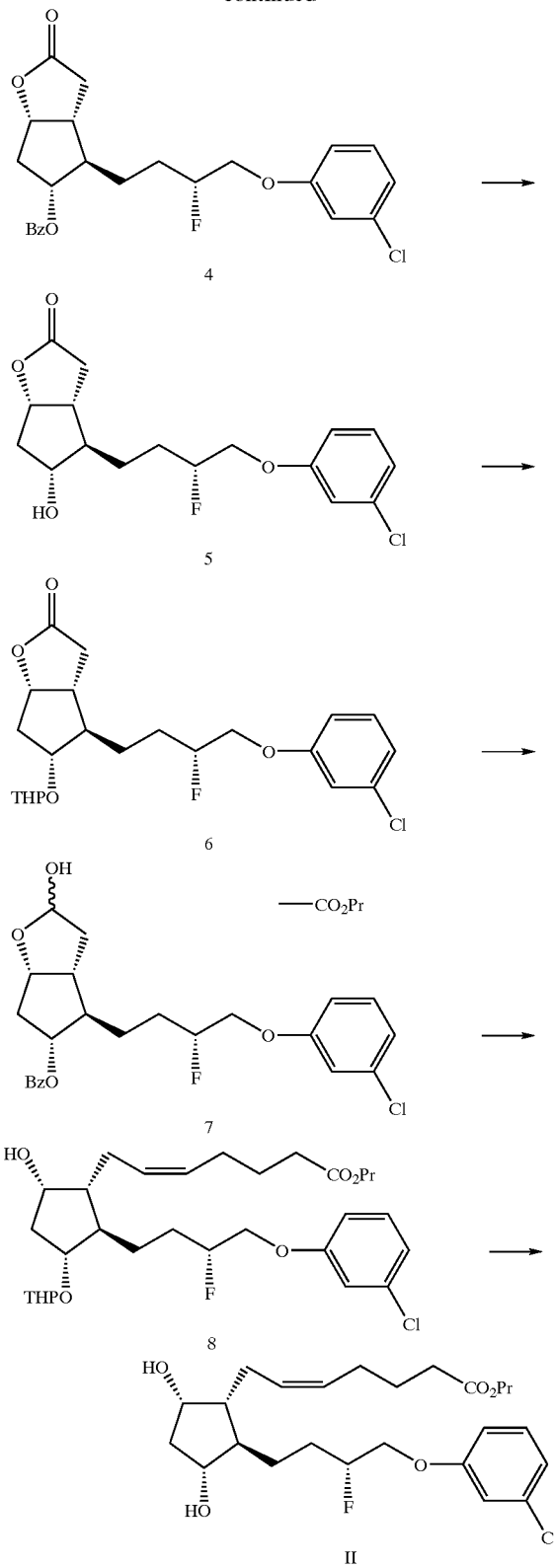

A. [3aR,4R(1E,3S),5R,6aS]-5-Benzoyloxy-4-[4-(3-chlorophenoxy)-3-hydroxy-1-butenyl]-hexahydro-2H-cyclopenta[b]furan-2-one (2)

To a solution of [3aR,4R(1E), 5R, 6aS]-5-benzoyloxy-4-[4-(3-chlorophenoxy)-3-oxo-1-butenyl]-hexahydro-2H-cyclopenta[b]furan-2-one (1; for preparation, see published European Patent Application EP 639563 A2, which is incorporated herein by this reference) (1.02 g, 2.32 mmol) in THF (10 mL) at −23° C. (bath temperature) was added dropwise a solution of (+)-B-chlorodiisopinocampheylborane (available from Aldrich Chemical Co., Milwaukee, Wis.) (1.4 g, 4.4 mmol) in THF (10 mL). The mixture was then warmed to 0° C. (bath temperature) and was quenched after 90 min by the addition of methanol (10 mL). Saturated NH$_4$Cl was added (35 mL), the mixture was extracted with ethyl acetate (3×40 mL), dried (MgSO$_4$), filtered, concentrated, and chromatographed on a 30 cm tall×41 mm diameter silica gel column eluting with 1:1 ethyl acetate:hexane to afford 2 (502 mg, 49%) as well as a mixture of 2 and its epimeric alcohol (254 mg, 23%).

B. [3aR,4R(3S),5R,6aS]-5-Benzoyloxy-4-[4-(3-chlorophenoxy)-3-hydroxybutyl]-hexahydro-2H-cyclopenta[b]furan-2-one (3)

A solution of 2 (500 mg, 1.14 mmol) and 10% w/w Pd/C (200 mg) in ethyl acetate (18 mL) was stirred under 1 atm of H$_2$ for 5.5 h, filtered through Celite, and concentrated to afford 3 (486 mg, 97%).

C. [3aR,4R(3R),5R,6aS]-5-Benzoyloxy-4-[4-(3-chlorophenoxy)-3-fluorobutyl]-hexahydro-2H-cyclopenta[b]furan-2-one (4)

To a solution of 3 (480 mg, 1.08 mmol) in CH$_2$Cl$_2$ (10 mL) at 0° C. (bath T) was added (diethylamino)sulfur trifluoride (DAST) available from Aldrich Chemical Co., Milwaukee, Wis. (450 mg, 2.8 mmol). After 3 h, saturated sodium bicarbonate was added (20 mL), the layers were separated, extracted with CH$_2$Cl$_2$ (2×20 mL), dried (MgSO$_4$), filtered, and chromatographed on an 18 cm tall× 26 mm diameter silica gel column eluting with 1:1 ethyl acetate:hexane to afford 4 (117 mg, 33%) as well as a mixture of 4 and a by-product (44 mg). $^{13}$C NMR (CDCl$_3$) δ 176.57 (C), 166.04 (C), 159.03 (C), 134.93 (C), 133.34 (CH), 130.31 (CH), 129.62 (CH), 128.54 (CH), 121.54 (CH), 115.06 (CH), 113.07 (CH), 91.02 (d, J=171 Hz, CH), 84.27 (CH), 79.80 (CH), 69.60 (d, J=24 Hz, CH$_2$), 52.26 (CH), 43.59 (CH), 36.96 (d, J=76 Hz, CH$_2$), 29.34 (d, J=21 Hz, CH$_2$), 28.57 (CH$_2$).

D. [3aR,4R(3R),5R,6aS]-4-[4-(3-Chlorophenoxy)-3-fluorobutyl]-5-hydroxy-hexahydro-2H-cyclopenta[b]furan-2-one (5)

To a solution of 4 (117 mg, 0.26 mmol) in methanol (5 mL) was added K$_2$CO$_3$ (57 mg, 0.41 mmol). After 90, min saturated NH$_4$Cl was added (10 mL), the mixture was extracted with ethyl acetate (3×15 mL), dried (MgSO$_4$), filtered, and chromatographed on a 16 cm tall×26 mm diameter silica gel column eluting with ethyl acetate to afford 5 (60 mg, 67%).

E. [3aR,4R(3R),5R,6aS]-4-[4-(3-Chlorophenoxy)-3-fluorobutyl]-5-(tetrahydropyran-2-yloxy)-hexahydro-2H-cyclopenta[b]furan-2-one (6)

To a solution of 5 (59 mg, 0.17 mmol) and 3,4-dihydro-2H-pyran (25 mg, 0.30 mmol) in CH$_2$Cl$_2$ (2.5 mL) at 0° C. (bath temperature) was added p-toluenesulfonic acid monohydrate (8 mg, 0.04 mmol). After 1 h, NEt$_3$ was added (0.1 mL), saturated sodium bicarbonate was added (5 mL), the layers were separated, extracted with CH$_2$Cl$_2$ (3×5 mL), dried (MgSO$_4$), filtered, and chromatographed on an 11 cm tall×26 mm diameter silica gel column eluting with 1:1 ethyl acetate:hexane to afford 6 (59 mg, 82%).

F. [3aR,4R(3R),5R,6aS]-4-[4-(3-Chlorophenoxy)-3-fluorobutyl]-5-(tetrahydropyran-2-yloxy)-hexahydro-2H-cyclopenta[b]furan-2-ol (7)

To a solution of 6 (59 mg, 0.14 mmol) in toluene (2 mL) at −78° C. (bath temperature) was added dropwise a 1.5 M solution of diisobutylaluminum hydride in toluene (0.14 mL, 0.21 mmol). After 90 min, the reaction was quenched by the addition of 1:1 methanol:ethyl acetate (1 mL), warmed to room temperature, added to a saturated solution of sodium potassium tartarate (4 mL), and stirred until the emulsion broke. The layers were separated, extracted with ethyl acetate (3×5 mL), dried (MgSO$_4$), filtered, concentrated, and passed through a pipette plug of silica gel eluting with ethyl acetate to afford 7 (59 mg, 99%), which was used immediately in the following step.

G. (5Z)-(9S,11R,15 R)-16-(3-Chlorophenoxy)-15-fluoro-9-hydroxy-11-(tetrahydropyran-2-yloxy)-17,18,19,20-tetranor-5-prostenoic Acid Isopropyl Ester (8)

To a suspension of (4-carboxybutyl) triphenylphosphonium bromide (205 mg, 0.46 mmol) in THF (2.5 mL) at 0° C. (bath temperature) was added a 1 M solution of potassium t-butoxide in THF (0.88 mL, 0.88 mmol). After 15 min, a solution of 7 (59 mg) in THF (1 mL) was added. After 1 h, the reaction was quenched by the addition of saturated NH$_4$Cl (10 mL), extracted with ethyl acetate (3×10 mL), dried (MgSO$_4$), filtered, and concentrated to afford an oil. This oil was dissolved in acetone (4 mL), the solution was cooled to 0° C. (bath temperature), and DBU was added (106 mg, 0.7 mmol). After 20 min, isopropyl iodide was added, and the reaction was allowed to come to room temperature overnight. The mixture was added to saturated NH$_4$Cl (5 mL), extracted with ethyl acetate (3×5 mL), dried (MgSO$_4$), filtered, concentrated, and passed through a pipette plug of silica gel eluting with 1:1 ethyl acetate:hexane to afford 8 (147 mg) contaminated with triphenylphosphine oxide. The sample was used without further purification in the next step.

H. (5Z)-(9S,11R,15 R)-16-(3-Chlorophenoxy)-9,11-dihydroxy-15-fluoro-17,18,19,20-tetranor-5-prostenoic Acid Isopropyl Ester (II)

To a solution of impure 8 from above (147 mg) in isopropanol (4 mL) was added 12 M HCl (0.8 mL). After 90, min saturated sodium bicarbonate was added (10 mL), the mixture was extracted with ethyl acetate (4×10 mL), filtered, concentrated, and chromatographed on a 17 cm tall×10 mm diameter silica gel column eluting with 1:1 ethyl acetate: hexane to afford II (31 mg, 47% from lactol 7). $^{13}$C NMR (CDCl$_3$) δ 173.40 (C), 159.18 (C), 134.90 (C), 130.26 (CH), 129.81 (CH), 129.08 (CH), 121.41 (CH), 115.06 (CH), 113.13 (CH), 91.44 (d, J=172 Hz, CH), 78.65 (CH), 74.61 (CH), 69.91 (d, J=23 Hz, CH$_2$), 67.63 (CH), 52.57 (CH), 51.72 (CH), 42.66 (CH$_2$), 34.01 (CH$_2$), 30.05 (d, J=21 Hz, CH$_2$), 28.86 (CH$_2$), 28.78 (CH$_2$), 26.73 (d, J=10 Hz, CH$_2$), 24.90 (CH$_2$), 21.82 (CH$_3$). MS, m/z calcd. for C$_{25}$H$_{36}$O$_5$FClNa [(M+Na)$^+$], 493; found, 493.

EXAMPLE 2

Synthesis of III

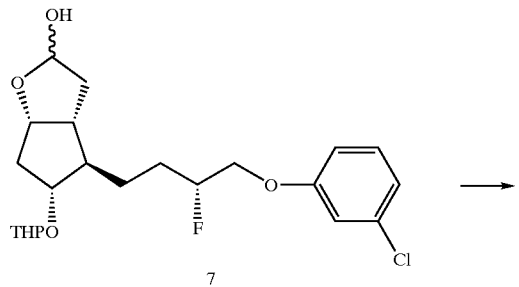

7

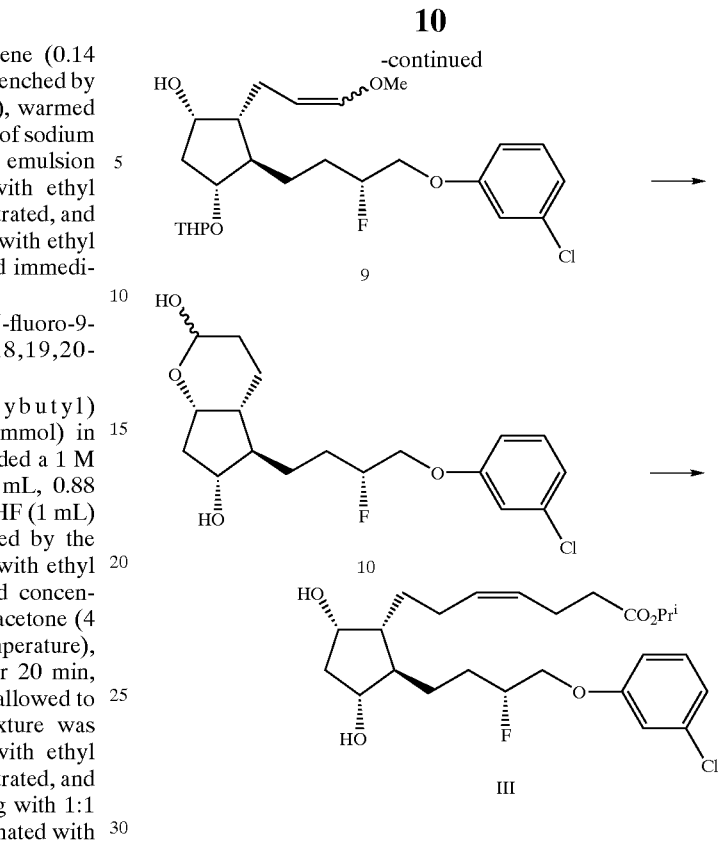

(4Z)-(9S,11R,15R)-16-(3-Chlorophenoxy)-9,11-dihydroxy-15-fluoro-17,18,19,20-tetranor-4-prostenoic Acid Isopropyl Ester (III)

Wittig condensation of 7 with Ph$_3$P$^+$CH$_2$OMe Cl$^-$ in the the presence of KOBu$^t$ in THF yields enol ether 9. Acidic hydrolysis using TsOH in THF/water gives lactol 10, which is reacted with Ph$_3$P$^+$(CH$_2$)$_3$CO$_2$H Br$^-$ in the presence of KOBu$^t$ in THF, followed by treatment of an acetone solution of the resulting carboxylic acid with DBU and isopropyl iodide, to afford III.

Synthesis of IV

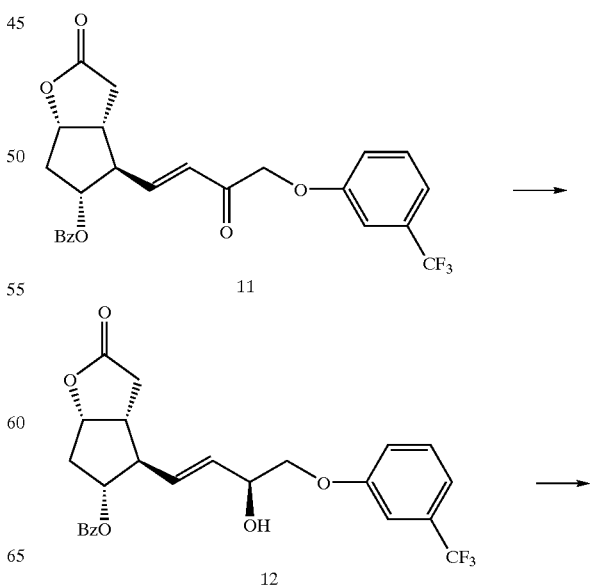

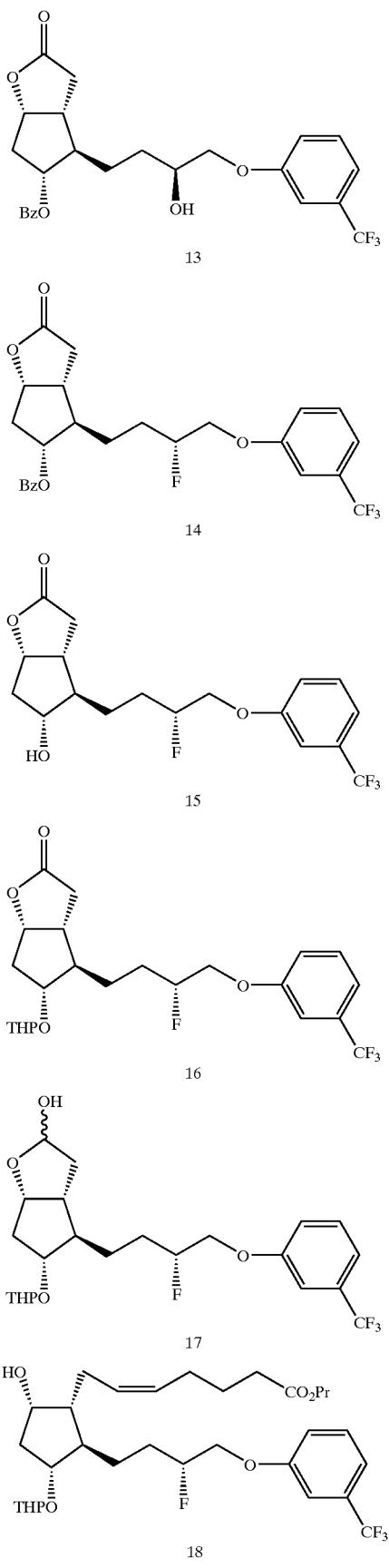

A. [3aR,4R(1E,3S),5R,6aS]-5-Benzoyloxy-4-[3-hydroxy-4-(3-(trifluoromethyl)phenoxy)-1-butenyl]-hexahydro-2H-cyclopenta[b]furan-2-one (12)

To a solution of [3aR,4R(1E),5R,6aS]-5-benzoyloxy-4-[3-oxo-4-(3-(trifluoromethyl)phenoxy)-1-butenyl]-hexahydro-2H-cyclopenta[b]furan-2-one (11; for preparation, see U.S. Pat. No. 4,321,275, which is incorporated by this reference) (1.77 g, 3.8 mmol) in THF (22 mL) at 0° C. (bath temperature) was added a solution of –(+)-B-chlorodiisopinocampheylborane (2.59 g, 8.1 mmol) in THF (37 mL). After 1 h, the reaction was warmed to room temperature, and, after 1 additional h, saturated sodium bicarbonate (30 mL) was added. The solution was extracted with ethyl acetate (3×30 mL), dried (MgSO$_4$), and filtered, and the residue was dissolved in 150 mL of 1:2 acetonitrile:hexane. The two-phase mixture was shaken in a separatory funnel and the bottom layer was concentrated. The residue was chromatographed on a 28 cm tall×41 mm diameter silica gel column eluting with 3:2 ethyl acetate:hexane to afford 12 (624 mg, 35%) as well as a mixture of 12 and the corresponding epimeric alcohol (681 mg, 39%).

B. [3aR,4R(3S),5R,6aS]-5-Benzoyloxy-4-[3-hydroxy-4-(3-(trifluoromethyl)phenoxy)-butyl]-hexahydro-2H-cyclopenta[b]furan-2-one (13)

A solution of 12 (600 mg, 1.29 mmol) and 10% Pd/C (77 mg) in ethyl acetate (15 mL) was stirred under 1 atm of H$_2$ for 3.5 h, filtered through Celite, and concentrated to afford 13 (601 mg, 100% yield).

C. [3aR,4R(3R),5R,6aS]-5-Benzoyloxy-4-[3-fluoro-4-(3-(trifluoromethyl)phenoxy)butyl]-hexahydro-2H-cyclopenta[b]furan-2-one (14)

To a solution of 13 (600 mg, 1.29 mmol) in CH$_2$Cl$_2$ (10 mL) at 0° C. (bath T) was added DAST (340 mg, 2.1 mmol). After 50 min, saturated sodium bicarbonate was added (15 mL), the layers were separated, extracted with CH$_2$Cl$_2$ (2×15 mL), dried (MgSO$_4$), filtered, and chromatographed on an 30 cm tall×41 mm diameter silica gel column eluting with 4:1 diethyl ether:hexane to afford 14 (312 mg, 50%). $^{13}$C NMR (CDCl$_3$) (partial spectrum) δ 91.10 (d, J=172 Hz, CH), 84.32 (CH), 79.88 (CH), 69.67 (d, J=23 Hz, CH$_2$), 52.25 (CH), 43.55 (CH), 36.93 (d, J=75 Hz, CH$_2$), 29.36 (CH$_2$), 28.71 (d, J=11 Hz, CH$_2$), 28.41 (CH$_2$).

D. [3aR,4R(3R),5R,6aS]-4-[3-Fluoro-4-(3-(trifluoromethyl)phenoxy)butyl]-5-hydroxy-hexahydro-2H-cyclopenta[b]furan-2-one (15)

To a solution of 14 (310 mg, 0.64 mmol) in methanol (10 mL) was added K$_2$CO$_3$ (128 mg, 0.93 mmol). After 2.5 h, saturated citric acid was added (20 mL), the mixture was extracted with ethyl acetate (3×20 mL), dried (MgSO$_4$), filtered, and chromatographed on a 14 cm tall×26 mm diameter silica gel column eluting with 3:2 ethyl acetate:hexane to afford 15 (197 mg, 82%).

E. [3aR,4R(3R),5R,6aS]-4-[3-Fluoro-4-(3-(trifluoromethyl)phenoxy)butyl]-5-(tetrahydropyran-2-yloxy)-hexahydro-2H-cyclopenta[b]furan-2-one (16)

To a solution of 15 (191 mg, 0.51 mmol) and 3,4-dihydro-2H-pyran (64 mg, 0.77 mmol) in CH$_2$Cl$_2$ (3.2 mL) at 0° C.

(bath temperature) was added p-toluenesulfonic acid monohydrate (60 mg, 0.31 mmol). After 25 min, NEt₃ was added (0.2 mL), saturated sodium bicarbonate was added (20 mL), the layers were separated, extracted with ethyl acetate (2×20 mL), dried (MgSO₄), filtered, and chromatographed on an 14 cm tall×26 mm diameter silica gel column eluting with 3:2 ethyl acetate:hexane to afford 16 (224 mg, 95%).

F. [3aR,4R(3R),5R,6aS]-4-[3-Fluoro-4-(3-(trifluoromethyl)phenoxy)butyl]-5-(tetrahydropyran-2-yloxy)-hexahydro-2H-cyclopenta[b]furan-2-ol (17)

To a solution of 16 (220 mg, 0.48 mmol) in toluene (4 mL) at −78° C. (bath temperature) was added dropwise a 1.5 M solution of diisobutylaluminum hydride in toluene (0.48 mL, 0.72 mmol). After 30 min, the reaction was quenched by the addition of 1:1 methanol:ethyl acetate (3 mL), warmed to room temperature, added to a saturated solution of sodium potassium tartarate (20 mL), and stirred until the emulsion broke. The layers were separated, extracted with ethyl acetate (2×20 mL), dried (MgSO₄), filtered, and concentrated to afford 17 (220 mg, 100%), which was used immediately in the following step.

G. (5Z)-(9S,11R,15 R)-15-Fluoro-9-hydroxy-11-(tetrahydropyran-2-yloxy)-16-[3-(trifluoromethyl)phenoxy]-17,18,19,20-tetranor-5-prostenoic Acid Isopropyl Ester (18)

To a suspension of (4-carboxybutyl)triphenylphosphonium bromide (750 mg, 1.7 mmol) in THF (5 mL) at 0° C. (bath temperature) was added a 1 M solution of potassium t-butoxide in THF (3.0 mL, 3.0 mmol). After 10 min, a solution of 17 (220 mg) in THF (3 mL) was added. After 90 min, the reaction was quenched by the addition of saturated NH₄Cl (20 mL), extracted with ethyl acetate (3×20 mL), dried (MgSO₄), filtered, and concentrated to afford an oil. This oil was dissolved in acetone (11 mL), the solution was cooled to 0° C. (bath temperature), and DBU was added (380 mg, 2.5 mmol). After 10 min, isopropyl iodide was added, and the reaction was allowed to come to room temperature overnight. The mixture was added to saturated NH₄Cl (15 mL), extracted with ethyl acetate (3×20 mL), dried (MgSO₄), filtered, concentrated, and chromatographed on a 14 cm tall×26 mm diameter silica gel column eluting with 3:2 hexane:ethyl acetate to afford 18 (147 mg, 52%).

H. (5Z)-(9S,11R,15 R)-9,11-Dihydroxy-15-fluoro-16-[3-(trifluoromethyl)phenoxy]-17,18,19,20-tetranor-5-prostenoic Acid Isopropyl Ester (IV)

To a solution of 18 (146 mg) in isopropanol (6 mL) was added 12 M HCl (0.4 mL). After 3.5 h, saturated sodium bicarbonate was added (10 mL), the mixture was extracted with ethyl acetate (2×10 mL), filtered, concentrated, and chromatographed on a 17 cm tall×26 mm diameter silica gel column eluting with a 3:2 ethyl acetate:hexane to straight ethyl acetate gradient to afford IV (92 mg, 73%). ¹³C NMR (CDCl₃) (partial spectrum) δ 91.44 (d, J=172 Hz, CH), 78.60 (CH), 74.54 (CH), 69.97 (d, J=23 Hz, CH₂), 67.64 (CH), 52.49 (CH), 51.70 (CH), 42.66 (CH₂), 34.01 (CH₂), 30.01 (d, J=21 Hz, CH₂), 28.84 (CH₂), 28.77 (CH₂), 26.70 (d, J=9 Hz, CH₂), 24.89 (CH₂), 21.79 (CH₃). MS, m/z calcd. for C₂₆H₃₇O₅F₄ [(M+H)⁺], 505.25706; found, 505.25705.

EXAMPLE 4

Synthesis of V

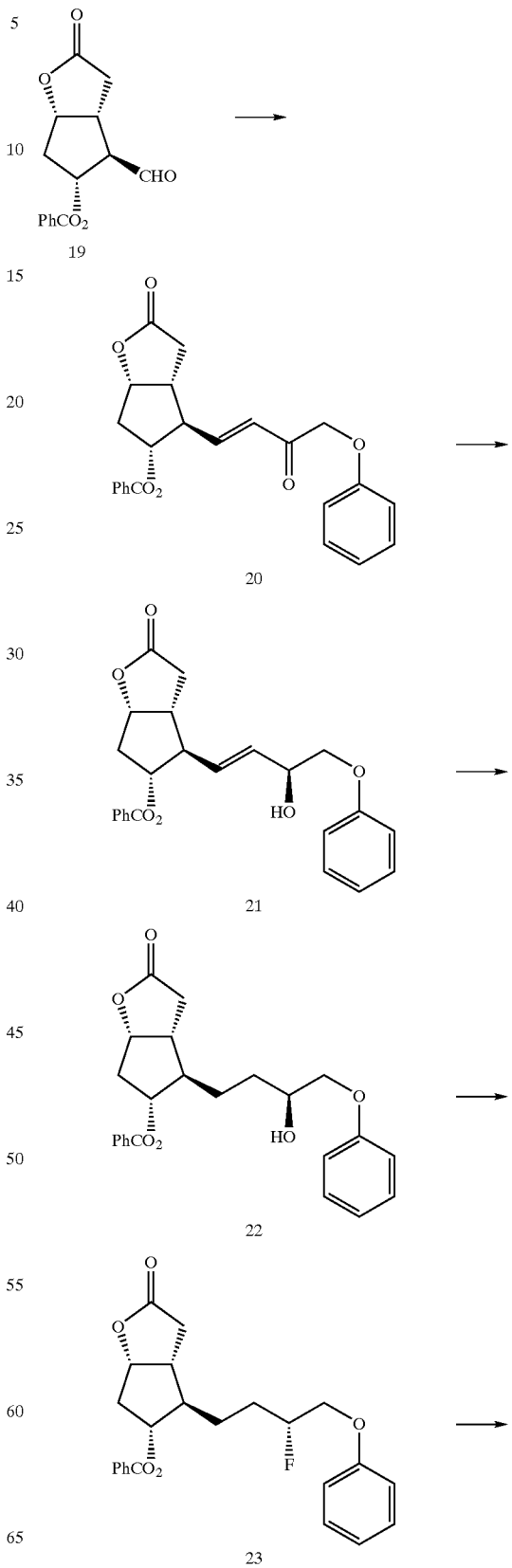

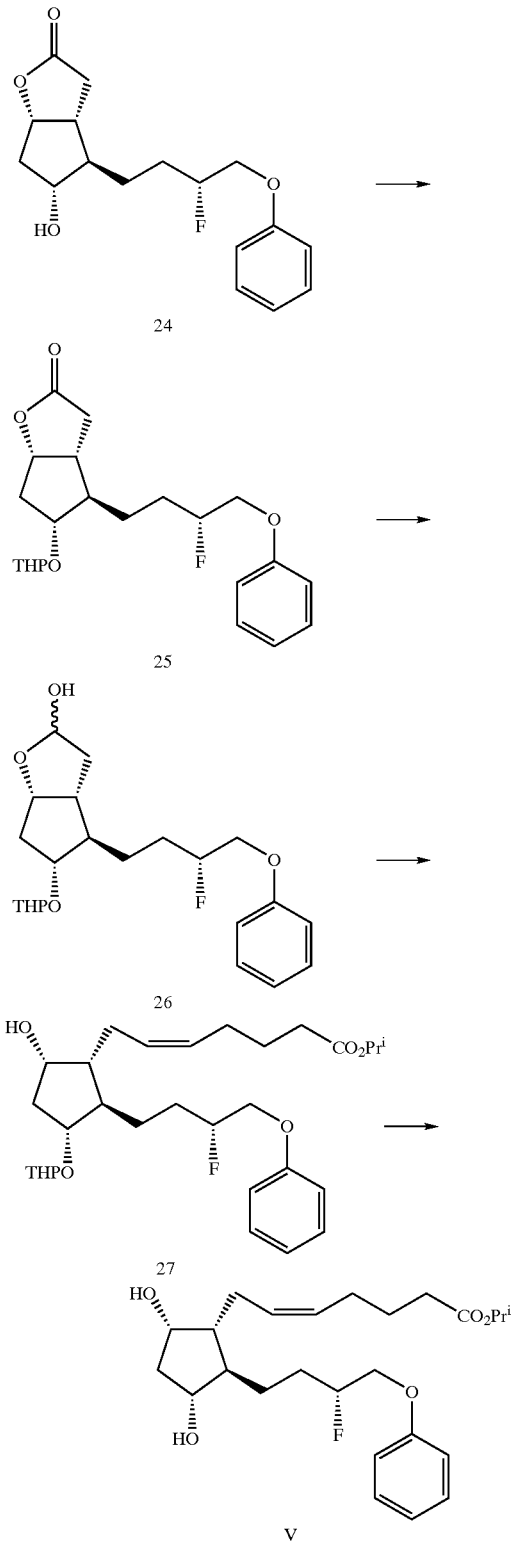

A. [3aR,4R(1E),5R,6aS]-5-benzoyloxy-4-(3-oxo-4-phenoxybutenyl)-hexahydro-2H-cyclopenta[b]furan-2-one (20)

A solution of [3aR,4R(1E),5R,6aS]-5-benzoyloxy-4-formyl-hexahydro-2H-cyclopenta[b]furan-2-one (19) (available from Cayman Chemical Company, Ann Arbor, Mich.) (8.00 g, 29.2 mmol) in dichloromethane (50 mL) was added to a 0° C. (bath temperature) suspension of dimethyl (3-phenoxy-2-oxopropyl)phosphonate (prepared in a manner analogous to that described in U.S. Pat. No. 5,665,773 for dimethyl (2-oxo-3-(3-chlorophenoxy)propyl) phosphonate, which patent is incorporated herein by this reference) (8.29 g, 32.1 mmol), lithium chloride (1.37 g, 35.04 mmol) and triethylamine (4.64 ml, 33.3 mmol) in THF (100 mL) with mechanical stirring for three hours. The reaction was quenched with aqueous 2 N hydrochloric acid (50 mL) and water (100 mL). The mixture was extracted with dichloromethane (200 ml and then 100 mL). The combined organic layers were washed with brine (100 mL), dried over magnesium sulfate and evaporated to a yellow oil. The resulting residue was purified by chromatography using silica gel and dichloromethane/ethyl acetate (8:2) to afford 20 as a white solid, 9.17 g (mp 120–5° C.). MS, m/z calcd. for $C_{24}H_{22}O_6Na$ [(M+Na)$^+$], 429; found, 429.

B. [3aR,4R(1E,3S),5R,6aS]-5-(Benzoyloxy)-4-[3-hydroxy-4-phenoxybutenyl]-hexahydro-2H-cyclopenta[b]furan-2-one (21)

A solution of 20 (8.16 g, 20 mmol) in THF (100 mL) was cooled to 0° C. (bath temperature) and treated with (+)-B-chlorodiisopinocampheylborane (12.8 g, 40 mmol). The reaction was warmed to room temperature and stirred overnight. The reaction was re-cooled to 0° C. and quenched with acetone (44 ml, 600 mmol) with stirring for one hour. Then methanol (50 mL) was added and the mixture was stirred for fifteen minutes. After the solvent was evaporated the residue was taken up in acetonitrile (100 mL) and washed with hexane (100 mL). The acetonitrile solution was passed through a pad of silica gel and evaporated, and the residue was purified by chromatography on silica gel eluting with hexane/ethyl acetate/dichloromethane (35:65:5) to afford 21 as a colorless oil (1.56 g, 19%). MS, m/z calcd. for $C_{24}H_{24}O_6$ [(M+Na)$^+$], 431; found, 431.

C. [3aR,4R(3S),5R,6aS]-5-(Benzoyloxy)-4-[3-hydroxy-4-phenoxybutyl]-hexahydro-2H-cyclopenta[b]furan-2-one (22)

A solution of 21 (1.55 g, 3.8 mmol) in ethyl acetate (50 mL) was treated with 10% Pd/C (200 mg) with shaking under hydrogen (50–60 psi) for 8 hours. The reaction was filtered through celite and the solvent was evaporated to provide 22 as a colorless oil (1.51 g, 97%). MS, m/z calcd. for $C_{24}H_{24}O_6Na$ [(M+Na)$^+$], 433; found, 433.

D. [3aR,4R(3R),5R,6aS]-5-(Benzoyloxy)-4-[3-fluoro-4-phenoxybutyl]-hexahydro-2H-cyclopenta[b]furan-2-one (23)

A 0° C. (bath temperature) solution of 22 (1.50 g, 3.65 mmol) in dichloromethane (40 mL) was treated with DAST (0.72 ml, 5.48 mmol) and stirred for 30 min. The reaction was slowly quenched with saturated aqueous sodium bicarbonate until bubbling ceased and then the mixture was poured into saturated aqueous sodium bicarbonate (100 mL). The organic layer was collected and washed with brine (100 mL), dried over magnesium sulfate, and evaporated to a yellow oil. This residue was purified by chromatography on silica gel eluting with hexane/ethyl acetate (8:2→7:3) to yield 23 as a colorless oil (300 mg, 20%). MS, m/z calcd. for $C_{24}H_{25}O_5FNa$ [(M+Na)$^+$], 435; found, 435.

E. [3aR,4R(3R),5R,6aS]-4-[3-Fluoro-4-phenoxybutyl]-5-hydroxy-hexahydro-2H-cyclopenta[b]furan-2-one (24)

A solution of 23 (0.30 g, 0.73 mmol) in methanol (10 mL) was treated with potassium carbonate (0.10 g, 0.73 mmol) and stirred at room temperature overnight. The reaction was quenched with aqueous saturated ammonium chloride (100 mL) and was extracted with dichloromethane (100 mL). The organic layer was washed with brine (100 mL), dried over magnesium sulfate, and evaporated to afford 24 as a colorless oil (170 mg, 77%).

F. [3aR,4R(3R),5R,6aS]-4-[3-Fluoro-4-phenoxybutyl]-5-(tetrahydropyran-2-yloxy)-hexahydro-2H-cyclopenta[b]furan-2-one (25)

To a 0° C. (bath temperature) solution of 24 (170 mg, 0.56 mmol) in dichloromethane (10 mL) was added 3,4-dihydro-2H-pyran (1.1 M in dichloromethane, 0.70 ml, 0.77 mmol) and p-toluenesulfonic acid monohydrate (10 mg). After stirring for 1 h, the reaction was quenched with triethylamine (1 mL) and saturated aqueous sodium bicarbonate (100 mL). The mixture was extracted with dichloromethane (100 mL), the organic layer was washed with brine (100 mL), dried over magnesium sulfate and evaporated to a colorless oil. The residue was purified by chromatography on silica gel eluting with hexane/ethyl acetate (1:1) to give 25 as a colorless oil (140 mg, 70%).

G. [2RS,3aR,4R(3R),5R,6aS]-4-[3-Fluoro-4-phenoxybutyl]-5-(tetrahydropyran-2-yloxy)-hexahydro-2H-cyclopenta[b]furan-2-ol (26)

A solution of 25 (140 mg, 0.39 mmol) in THF (10 mL) was cooled to −78° C. (bath temperature) and treated with diisobutylaluminum hydride (1 M in hexanes, 0.63 ml, 0.63 mmol). After stirring for 2 h, the reaction was quenched with saturated aqueous potassium sodium tartrate (100 mL) and stirred at room temperature overnight. The mixture was extracted with dichloromethane (100 ml×2), and the combined organic layers were washed with brine (100 mL), dried over magnesium sulfate, and evaporated. The residue was purified by chromatography on silica gel eluting with hexane/ethyl acetate (1:1) to provide 26 as a colorless oil (120 mg, 92%). MS, m/z calcd. for $C_{22}H_{31}O_5FNa$ [(M+Na)$^+$], 417; found, 417.

H. (5Z)-(9S,11R,15R)-15-Fluoro-9-hydroxy-11-(tetrahydropyran-2-yloxy)-17,18,19,20-tetranor-5-prostenoic Acid Isopropyl Ester (27)

A solution of 26 (0.11 g, 0.28 mmol) in THF (15 mL) was added to an ice bath-cooled suspension of $Ph_3P^+(CH_2)_4CO_2H\ Br^-$ (0.31 g, 0.70 mmol) in THF (10 mL) containing potassium t-butyloxide (1 M in THF, 1.4 ml, 1.4 mmol). The reaction was stirred in the ice bath for 30 min and at room temperature for two days. The reaction was quenched with aqueous saturated ammonium chloride (100 mL) and adjusted to pH 4-5 with acetic acid. The mixture was extracted with dichloromethane (100 ml×2). The combined organic layers were washed with brine (100 ml×2), dried over sodium sulfate, and evaporated. The residue (0.35 g) was taken up in acetone (10 mL) and sequentially treated with DBU (0.43 ml, 2.8 mmol) and isopropyl iodide (1.3 ml, 2.8 mmol), and was stirred overnight. The reaction was quenched with saturated aqueous ammonium chloride (100 mL). The mixture was extracted with dichloromethane (100 mL) and the organic layer was dried over magnesium sulfate and evaporated. The residue was purified by chromatography using silica gel and hexane/ethyl acetate (1:1) to afford 27 as a colorless oil (50.4 mg, 33%).

I. (5Z)-(9S,11R,15R)-9,11-Dihydroxy-15-fluoro-17,18,19,20-tetranor-5-prostenoic Acid Isopropyl Ester (V)

A solution of 27 (50 mg, 0.094 mmol) in isopropanol (5 mL) was treated with 2 N hydrochloric acid (2 ml) and stirred for 3.5 h. The reaction was quenched with saturated aqueous sodium bicarbonate (100 mL) and extracted with dichloromethane (100 mL). The organic layer was washed with brine (100 mL), dried over magnesium sulfate, filtered, and evaporated. The residue was purified by chromatography on silica gel eluting with hexane/ethyl acetate (7:3→1:1→0:1) to afford V as a colorless oil (29 mg, 71%). $^{13}$C NMR (CDCl$_3$) δ 173.4 (C), 158.4 (C), 129.8 (CH), 129.5 (CH), 129.1 (CH), 121.2 (CH), 114.6 (CH), 93.4 (CH), 89.9 (CH), 78.9 (CH), 74.7 (CH), 69.8 (CH$_2$), 69.4 (CH$_2$), 67.6 (CH), 52.7 (CH), 51.7 (CH), 42.6 (CH$_2$), 34.0 (CH$_2$), 30.4 (CH$_2$), 29.9 (CH$_2$), 28.9 (CH$_2$), 28.8 (CH$_2$), 26.9 (CH$_2$), 26.6 (CH$_2$), 24.9 (CH$_2$), 21.8 (CH$_3$). MS, m/z calcd. for $C_{25}H_{37}O_5FNa$ [(M+Na)$^+$], 459; found, 459.

EXAMPLE 5

Synthesis of Compound VI

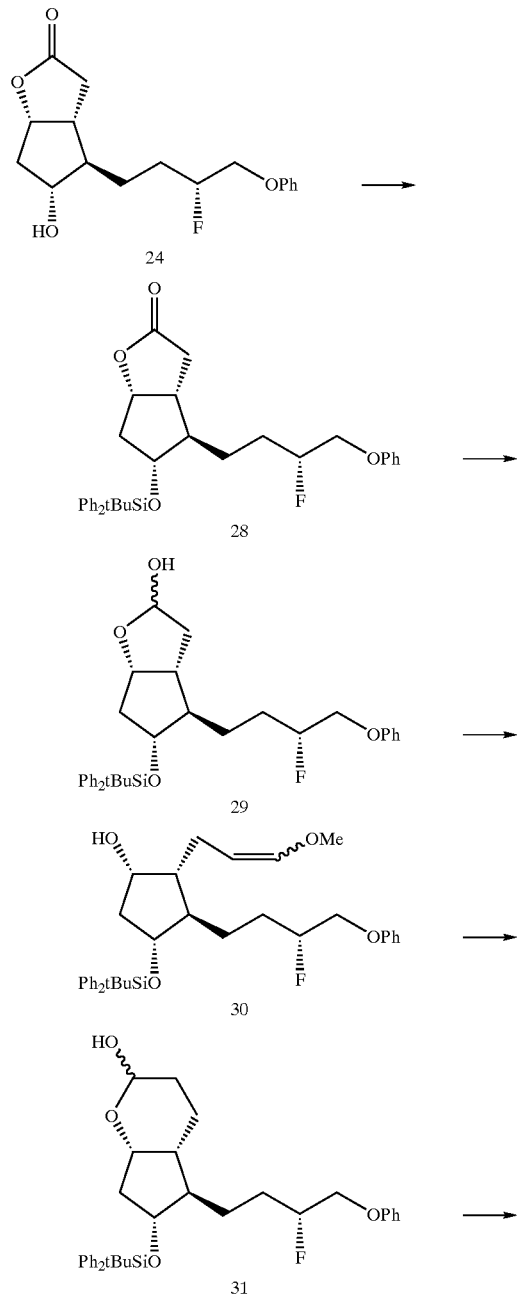

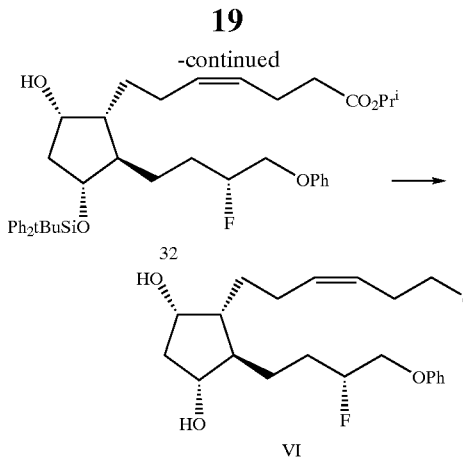

[3aR,4R(3R),5R,6aS]-5-(t-Butyldiphenylsiloxy)-4-(3-fluoro-4-phenoxybutyl)-hexahydro-2H-cyclopenta[b]furan-2-one (28)

To a mixture of alcohol 24 and its corresponding 15-desfluoro-$\Delta^{14,15}$ olefin (312 mg or 1.01 mmol calculated as the fluoride), CH$_2$Cl$_2$ (10 mL), DMAP (35 mg, 0.29 mmol), and imidazole (109 mg, 1.60 mmol) was added $^t$BuPh$_2$SiCl (360 mg, 1.31 mmol). After 3 h, saturated NaCl was added (10 mL), the layers were separated, the aqueous phase was extracted with CH$_2$Cl$_2$ (2×10 mL), and the combined organic layers were dried (MgSO$_4$), filtered, and concentrated. The residue was purified by chromatography on a 20 cm tall×26 mm diameter silica gel column eluting with 20% ethyl acetate in hexane to afford pure (as measured by $^1$H NMR spectroscopy) 28 (213 mg, 39% yield), as well as a 65:35 molar mixture of 28 to its corresponding 15-desfluoro-$\Delta^{14,15}$ olefin [246 mg; total yield of silylated products=213 mg+246 mg=459 mg=83%, when calculated as if all of the sample were the 15-fluoride; yield of silylated 15-fluoride itself=(213 mg+(0.65*246 mg))=(213 mg+160 mg)=373 mg]. $^{13}$C NMR (50 MHz) δ177.20 (C), 158.31 (C), 135.95 (CH), 135.91 (CH), 133.47 (CH), 133.35 (C), 129.83 (CH), 129.79 (CH), 129.52 (CH), 127.72 (CH), 127.67 (CH), 121.30 (CH), 114.49 (CH), 91.38 (d, J=172 Hz, CH), 84.30 (CH), 78.53 (CH), 69.17 (d, J=24 Hz, CH$_2$), 54.98 (CH), 42.92 (CH), 40.17 (CH$_2$), 36.30 (CH$_2$), 29.36 (d, J=21 Hz, CH$_2$), 28.29 (d, J=4 Hz, CH$_2$), 26.80 (CH$_3$), 18.93 (C). HRMS, m/z calculated for C$_{33}$H$_{39}$O$_4$SiFNa [(M+Na)$^+$], 569.249528; found, 569.24951.

[2RS,3aR,4R(3R),5R,6aS]-5-(t-Butyldiphenylsiloxy)-4-(3-Fluoro-4-phenoxybutyl)-hexahydro-2H-cyclopenta[b]furan-2-ol (29)

To a solution of a mixture of 29 and its corresponding 15-desfluoro-$\Delta^{14,15}$ olefin (645 mg or 1.18 mmol calculated as the fluoride) in toluene (12 mL) at −78° C. was added dropwise a 1.5 M solution of DIBAL-H in toluene (1.8 mL, 2.7 mmol). After 30 min, methanol (1 mL) was added and the reaction was warmed to room temperature. Saturated NH$_4$Cl (5 mL) and sodium potassium tartrate (9 mL) were added, and the mixture was stirred until the emulsion broke (about 20 min). The solution was extracted with ethyl acetate (2×25 mL) and the combined organic layers were dried (MgSO$_4$), filtered, and concentrated. The residue was then purified by chromatography on a 10 cm tall×26 mm diameter silica gel column eluting with 40% ethyl acetate in hexane to afford lactol 29 as a mixture with its corresponding 15-desfluoro-$\Delta^{14,15}$ olefin (523 mg, 81% nominal yield). HRMS, m/z calcd. for C$_{33}$H$_{41}$O$_4$SiFNa [(M+Na)$^+$], 571.266039; found, 571.26605.

(1EZ)-(9S,11R,15R)-11-(t-Butyldiphenylsiloxy)-15-fluoro-9-hydroxy-16-phenoxy-3,4,5,6,17,18,19,20-octanor-1-prosten-1-yl Methyl Ether (30)

To a suspension of Ph$_3$P$^+$CH$_2$OCH$_3$Cl$^−$ (1.05 g, 3.07 mmol) and KOBu$^t$ (1 M in THF, 2.85 mL, 2.85 mmol) in THF (8 mL) at 0° C. was added a solution of 29 (516 mg of 29 as a mixture with its corresponding 15-desfluoro-$\Delta^{14,15}$ olefin, 0.94 mmol nominal fluoride) in THF (11 mL). After 15 min saturated KH$_2$PO$_4$ (10 mL), saturated NaCl (25 mL), and water (15 mL) were added, the mixture was extracted with ethyl acetate (2×50 mL), and the combined organic layers were dried (MgSO$_4$), filtered, and concentrated. The residue was purified by chromatography on an 18 cm tall×26 mm diameter silica gel column eluting with 20% ethyl acetate in hexane to afford 30 as a mixture with its corresponding 15-desfluoro-$\Delta^{14,15}$ olefin (408 mg, 75% nominal yield). HRMS, m/z calcd. for C$_{35}$H$_{45}$O$_4$SiFNa [(M+Na)$^+$], 599.296403; found, 599.29638.

[2RS,4aR,5R(3R),6R,7aS]-6-(t-Butyldiphenylsiloxy)-5-(3-Fluoro-4-phenoxybutyl)-octahydro-2H-cyclopenta[b]pyran-2-ol (31)

A solution of a mixture of 30 with its corresponding 15-desfluoro-$\Delta^{14,15}$ olefin (402 mg nominal or 0.700 mmol calculated as the fluoride), p-toluenesulfonic acid monohydrate (82 mg, 0.43 mmol), THF (10 mL), and water (1 mL) were heated to 65–70° C. (internal temperature). After 2 h, the reaction was cooled to room temperature, saturated NaHCO$_3$ (10 mL) and saturated NaCl (10 mL) were added, and the mixture was extracted with ethyl acetate (2×30 mL). The combined organic layers were dried (MgSO$_4$), filtered, and concentrated, and the residue was purified by chromatography on a 13 cm tall×26 mm diameter silica gel column eluting with a 20%→40% ethyl acetate in hexane gradient to afford pyran 31 as a mixture with its corresponding 15-desfluoro-$\Delta^{14,15}$ olefin (254 mg nominal, 64% yield calculated as the fluoride). HRMS, m/z calcd. for C$_{34}$H$_{43}$O$_4$SiFNa [(M+Na)$^+$], 585.281036; found, 585.28100.

(4Z)-(9S,11R,15R)-11-(t-Butyldiphenylsiloxy)-15-fluoro-9-hydroxy-16-phenoxy-17,18,19,20-tetranor-4-prostenoic Acid Isopropyl Ester (32)

To a suspension of Ph$_3$P$^+$(CH$_2$)$_3$CO$_2$H Br$^−$ (585 mg, 1.36 mmol) in THF (3 mL) at 0° C. was added KOBu$^t$ (1.35 mL). An orange color developed, and after 15 min a THF (5 mL) solution of 31 as a mixture with its corresponding 15-desfluoro-$\Delta^{14,15}$ olefin (250 mg, 0.44 mmol calculated as the fluoride) was added. After 1 h an additional amount of KOBu$^t$ (0.8 mL) was added, and after 50 more min aqueous citric acid (0.76 M, 5 mL) and water (5 mL) were added. The mixture was extracted with ethyl acetate (2×20 mL) and then washed with water (1×15 mL), dried (Na$_2$SO$_4$), filtered, and concentrated to provide the crude Wittig product as a white foam.

The foam was dissolved in acetone (10 mL) and cooled to 0° C., and DBU (448 mg, 2.94 mmol) was added. After 30 min, isopropyl iodide (480 mg, 2.82 mmol) was added. The reaction was then warmed to room temperature and stirred overnight. After 18 h, additional portions of DBU (448 mg, 2.94 mmol) and isopropyl iodide (480 mg) were added, and the reaction was stirred for 72 h. Saturated KH$_2$PO$_4$ (15 mL) and saturated NaCl (15 mL) were added, and the mixture was extracted with ethyl acetate (3×25 mL), dried (MgSO$_4$), filtered, and concentrated. The residue was purified by chromatography on a 15 cm tall×26 mm diameter silica gel column eluting with 20% ethyl acetate in hexane to afford a mixture of olefin 32, its corresponding 15-desfluoro-$\Delta^{14,15}$ olefin, and Ph$_3$P$^+$(CH$_2$)$_3$CO$_2$Pr$^i$ Br$^−$ (503 mg total, >100% nominal yield). HRMS, m/z calcd. for $C_{41}H_{56}O_5SiF$ [(M+H)$^+$], 675.387994; found, 675.38800.

(4Z)-(9S,11R,15R)-9,11-Dihydroxy-15-fluoro-16-phenoxy-17,18,19,20-tetranor-4-prostenoic Acid Isopropyl Ester (VI)

To a solution of the above impure sample of 32 in THF (8 mL) was added a 1 M solution of TBAF in THF (0.85 mL, 0.85 mmol). After 3 h, saturated NH$_4$Cl (20 mL) was added, the mixture was extracted with ethyl acetate (3×20 mL), dried (MgSO$_4$), filtered, and concentrated. The residue was purified by chromatography on a 16 cm tall×26 mm diameter silica gel column eluting with 60% ethyl acetate in hexane to afford VI as a 2:1 molar mixture (as measured by $^{13}$C NMR spectroscopy) with its corresponding 15-desfluoro-$\Delta^{14,15}$ olefin (103 mg, 54% three-step yield from lactol 31, calculated as the 15-fluoride). The sample was further purified by HPLC on a chiral AD column using 4:1 hexane:isopropanol to afford the 15-desfluoro-$\Delta^{14,15}$ olefin geometrical isomers (4Z,14EZ)-(9S,11R)-9,11-Dihydroxy-16-phenoxy-17,18,19,20-tetranor-4,14-prostadienoic acid isopropyl ester as the minor, faster eluting component (16.8 mg) and the title compound VI as the major, slower-eluting component (67.3 mg). As measured by $^{13}$C NMR spectroscopy, this sample of VI consisted of a ~94:6 mixture of 4Z:4E olefin geometrical isomers. $^{13}$C NMR (150 MHz) δ173.02 (C), 158.39 (C), 131.07 (CH), 129.47 (CH), 127.68 (CH), 121.16 (CH), 114.55 (CH), 91.68 (d, J=171 Hz, CH), 78.54 (CH), 74.14 (CH), 69.58 (d, J=22 Hz, CH$_2$), 67.78 (CH), 52.92 (CH), 51.53 (CH), 42.58 (CH$_2$), 34.42 (CH$_2$), 30.10 (d, J=21 Hz, CH$_2$), 28.79 (CH$_2$), 28.74 (d, J=9 Hz, CH$_2$), 26.02 (CH$_2$), 22.69 (CH$_2$), 21.86 (CH$_3$), 21.79 (CH$_3$). HRMS, m/z calcd. for $C_{25}H_{38}O_5F$ [(M+H$^+$)], 437.270740; found, 437.27075.

The 15-fluoro PGF's of the present invention may be formulated in various pharmaceutical compositions for administering to humans and other animals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives thereof, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil) cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of substituted tetrahydrofurans of the present invention include the following Examples 6–10:

EXAMPLE 6

| Ingredient | Amount (wt %) |
| --- | --- |
| Compound II | 0.005 |
| Phosphate Buffered Saline | 1.0 |
| Polysorbate 80 | 0.5 |
| Purified water | q.s. to 100% |

EXAMPLE 7

| Ingredient | Amount (wt %) |
| --- | --- |
| Compound V | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 8

| Ingredient | Amount (wt %) |
| --- | --- |
| Compound III | 0.005 |
| Monobasic sodium phosphate | 0.05 |

-continued

| Ingredient | Amount (wt %) |
|---|---|
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 9

| Ingredient | Amount (wt %) |
|---|---|
| Compound III | 0.005 |
| Phosphate Buffered Saline | 1.0 |
| Hydroxypropyl-β-cyclodextrin | 4.0 |
| Purified water | q.s. to 100% |

EXAMPLE 10

| Ingredient | Amount (wt/v %) |
|---|---|
| Compound VI | 0.005 |
| Polyoxyl 40 Hydrogenated Castor Oil (HCO-40) | 0.5 |
| Tromethamine | 0.12 |
| Boric Acid | 0.3 |
| Mannitol | 4.6 |
| Edetate Disodium | 0.01 |
| Benzalkonium Chloride | 0.015 |
| NaOH/HCl | q.s. pH 6.0 ± 0.2 |
| Purified Water | q.s. 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

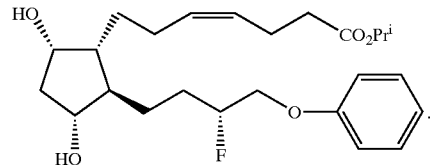

What is claimed is:

1. A method of treating glaucoma or ocular hypertension in a patient, which comprises administering to the patient a pharmaceutically effective amount of a compound of formula I:

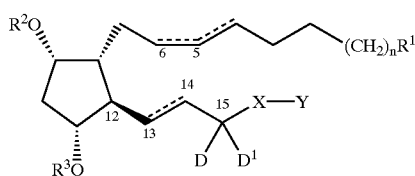

wherein:

$R^1$=$CO_2R$, $CONR^4R^5$, $CH_2OR^6$, or $CH_2NR^7R^8$; where R=H or cationic salt moiety, or $CO_2R$=ophthalmically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

- - - =a single bond between carbons 5 and 6, a cis double bond between carbons 4 and 5, and a single or trans double bond between carbons 13 and 14;

$R^2$, $R^3$=same or different=H, alkyl, or acyl;

D, $D^1$=different=H and fluorine;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=$(CH_2)_pY^1$; where p=0–6; and

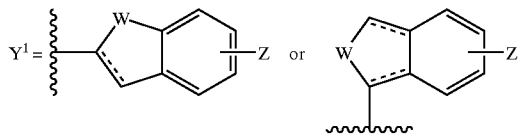

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and

- - - =single or double bond.

2. The method of claim 1, wherein the compound is administered topically.

3. The method of claim 2, wherein the compound is administered as a solution, suspension or emulsion.

4. The method of claim 1, wherein for the compound of formula I:

$R^1$=$CO_2R$, where R=H; or $CO_2R$=ophthalmically acceptable ester moiety, where R=alkyl;

n=0;

- - - =a single bond between carbons 5 and 6, a cis double bond between carbons 4 and 5, and a single or trans double bond between carbons 13 and 14;

$R^2$=$R^3$=H;

D=fluorine in the alpha (α) configuration, and $D^1$=H in the beta (β) configuration;

X=$CH_2O$ or $CH_2CH_2$; and

Y=phenyl, optionally substituted with halo or trihalomethyl.

5. The method of claim 2, wherein the concentration of the compound is between about 0.00003 to about 0.5 weight percent.

6. The method of claim 5, wherein the concentration of the compound is between about 0.0005 to about 0.03 weight percent.

7. The method of claim 6, wherein the concentration of the compound is between about 0.001 to about 0.01 weight percent.

8. The method of claim 5, wherein the compound is:

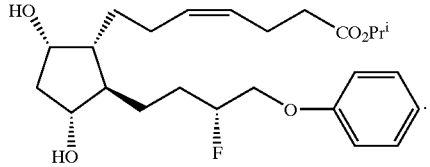

9. A compound of formula I:

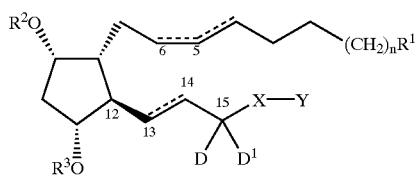

wherein:

$R^1=CO_2R$, $CONR^4R^5$, $CH_2OR^6$, or $CH_2NR^7R^8$; where R=H or cationic salt moiety or $CO_2R=$ pharmaceutically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

- - -=a single bond between carbons 5 and 6, a cis double bond between carbons 4 and 5, and a single or trans double bond between carbons 13 and 14;

$R^2$, $R^3$=same or different=H, alkyl, or acyl;

D, $D^1$=different=H and fluorine;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=$(CH_2)_pY^1$; where p=0–6; and

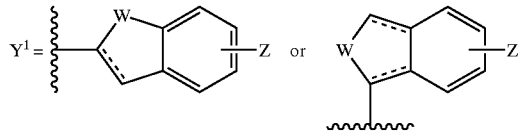

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and

- - -=single or double bond.

10. The compound of claim 9, wherein:

$R^1=CO_2R$, where R=H; or $CO_2R$=pharmaceutically acceptable ester moiety;

n=0;

- - -=a single bond between carbons 5 and 6, a cis double bond between carbons 4 and 5, and a single or trans double bond between carbons 13 and 14;

$R^2=R^3$=H;

D=fluorine in the alpha (α) configuration, and $D^1$=H in the beta (β) configuration;

X=$CH_2O$ or $CH_2CH_2$; and

Y=phenyl, optionally substituted with halo or trihalomethyl.

11. The compound of claim 10, wherein the pharmaceutically acceptable ester moiety is a carboxylic acid alkyl ester moiety.

12. The compound of claim 11, having the formula:

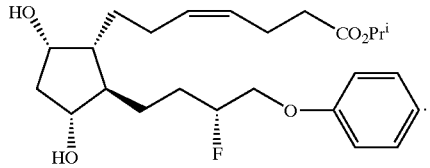

13. A topical ophthalmic composition for the treatment of glaucoma and ocular hypertension, comprising a compound of formula I:

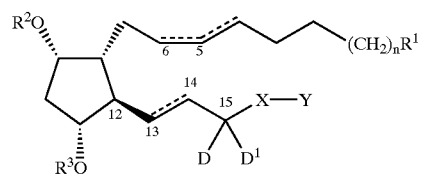

wherein:

$R^1=CO_2R$, $CONR^4R^5$, $CH_2OR^6$, or $CH_2NR^7R^8$; where R=H or cationic salt moiety, or $CO_2R$=ophthalmically acceptable ester moiety; $R^4$, $R^5$=same or different=H or alkyl; $R^6$=H, acyl, or alkyl; $R^7$, $R^8$=same or different=H, acyl, or alkyl; with the proviso that if one of $R^7$, $R^8$=acyl, then the other=H or alkyl;

n=0 or 2;

- - -=a single bond between carbons 5 and 6, a cis double bond between carbons 4 and 5, and a single or trans double bond between carbons 13 and 14;

$R^2$, $R^3$=same or different=H, alkyl, or acyl;

D, $D^1$=different=H and fluorine;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=$(CH_2)_pY^1$; where p=0–6; and

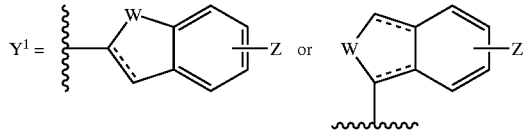

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and

- - -=single or double bond; and an ophthalmically acceptable vehicle therefor.

14. The composition of claim 13, wherein:

R¹=CO₂R, where R=H; or CO₂R=ophthalmically acceptable ester moiety;

n=0;

- - - =a single bond between carbons 5 and 6, a cis double bond between carbons 4 and 5, and a single or trans double bond between carbons 13 and 14;

R²=R³=H;

D=fluorine in the alpha (α) configuration, and D¹=H in the beta (β) configuration;

X=CH₂O or CH₂CH₂; and

Y=phenyl, optionally substituted with halo or trihalomethyl.

15. The composition of claim 14, wherein the ophthalmically acceptable ester moiety is a lower alkyl carboxylic acid alkyl ester moiety.

16. The composition of claim 15, wherein the compound is: